United States Patent [19]

Leuner et al.

[11] Patent Number: 4,665,926

[45] Date of Patent: May 19, 1987

[54] METHOD AND APPARATUS FOR MEASURING THE RELAXATION STATE OF A PERSON

[76] Inventors: Hanscarl Leuner, Eisenacher Str. 14, D-3400 Göttingen; Hartwig Klaumünzer, Egidienstr. 92, D-8520 Erlangen, both of Fed. Rep. of Germany

[21] Appl. No.: 799,158

[22] Filed: Nov. 18, 1985

[30] Foreign Application Priority Data

Nov. 17, 1984 [DE] Fed. Rep. of Germany ....... 3442174

[51] Int. Cl.⁴ .............................................. A61B 5/02
[52] U.S. Cl. .................................... 128/716; 128/671; 128/1 C
[58] Field of Search ............... 128/1 C, 716, 718, 719, 128/721, 722, 723, 724, 905, 671, 204.21, 205.3

[56] References Cited

U.S. PATENT DOCUMENTS

| | | | |
|---|---|---|---|
| 2,944,542 | 7/1960 | Barnett et al. ...................... | 128/671 |
| 3,219,028 | 11/1965 | Giordano ............................ | 128/1 C |
| 3,424,147 | 1/1969 | Giordano ............................ | 128/1 C |
| 3,433,217 | 3/1969 | Rieke .................................. | 128/723 |
| 3,572,317 | 3/1971 | Wade .................................. | 128/723 |
| 3,798,629 | 3/1974 | La Taillade et al. ............... | 128/716 |
| 3,871,360 | 3/1975 | Van Horn et al. .................. | 128/671 |
| 4,289,142 | 9/1981 | Kearns ................................ | 128/716 |
| 4,368,740 | 1/1983 | Binder ................................ | 128/718 |
| 4,463,764 | 8/1984 | Anderson et al. .................. | 128/719 |

FOREIGN PATENT DOCUMENTS

| | | |
|---|---|---|
| 7407730 | 5/1974 | Fed. Rep. of Germany . |
| 7600359 | 7/1976 | Fed. Rep. of Germany . |
| 3109026 | 9/1982 | Fed. Rep. of Germany . |
| 1359005 | 7/1974 | United Kingdom . |
| 1492875 | 11/1977 | United Kingdom . |

*Primary Examiner*—Edward M. Coven
*Attorney, Agent, or Firm*—Karl F. Ross; Herbert Dubno

[57] ABSTRACT

In a system for respiratory feedback therapy, relaxation state can be qualitatively measured by forming a quotient between values related to the inhalation/exhalation duration and values related to the pause between inhalation/exhalation phases over intervals of 0.5 to 3 minutes or 5 to 20 respiration cycles.

15 Claims, 7 Drawing Figures

METHOD AND APPARATUS FOR MEASURING THE RELAXATION STATE OF A PERSON

FIELD OF THE INVENTION

Our present invention relates to a method of and to an apparatus for measuring the relaxation state of a person by monitoring respiration and, more particularly, to a method of and to an apparatus for measuring the relaxation state in such fashion that reproducible results which can be used, for example, in relaxation therapy can be obtained.

BACKGROUND OF THE INVENTION

Biofeedback approaches have been employed in relaxation therapy utilizing, for example, the respiratory movements of a patient or subject as the monitored variable by which a feedback is provided to the individual so that respiration can be controlled and, as a consequence, a relaxation state can be induced.

In this technique, described, for example, in German patent document DE-OS No. 31 09 026 of May 15, 1984, or the attached brochure relating to respiratory feedback issued by Gesellschaft für Medizinische Feedback-Geräte GmbH, Göttingen, Germany, and in British Pat. Nos. 1,359,005 and 1,492,875 and German Utility Models DB GM Nos. 7 407 730 and 7 600 359, the respiratory movements of the subject are detected, these movements are transformed into amplified signals by appropriate transducers or electrical circuitry and these respiration and sensing signals are utilized in turn to generate optical or acoustical signals which are applied in a feedback loop to the patient.

This respiratory feedback process can be utilized to generate a relaxed state, i.e. to reduce muscle tone and to reduce brain activity.

However, a measurement of the relaxation state in some absolute or objective manner cannot be effected easily by conventional means. For example, if the relaxation state is to be determined by muscular relaxation, it has been necessary to use electromyelographs while, if the state is determined by brain wave activity, it has been necessary to use electroencephalograms.

Hence the procedures used heretofore for measuring the relaxation state of a patient have involved very expensive and complex equipment and instruments and, moreover, instruments which can only be used with special computers or calculating systems for transforming the electroencepholograph or electromyelograph reading into values representing the degree of relaxation.

OBJECTS OF THE INVENTION

It is, therefore, the principal object of the present invention to provide an improved method of easily, rapidly and inexpensively measuring the relaxation state of a patient, and changes in the relaxation state, whereby drawbacks of prior art techniques are avoided.

Yet another object of our invention is to provide an improved apparatus for measuring the relaxation state which is of substantially lower cost and frequently greater reliability and versatility than earlier systems proposed for the purpose.

Yet another object of the invention is to provide a method of and an apparatus for easily determining and registering the relaxation state of a patient undergoing respiratory feedback relaxation therapy which does not require body contact or intrusive methods or elements.

SUMMARY OF THE INVENTION

We have discovered that it is possible to obtain an objective measurement of the relaxation state of a subject undergoing respiratory relaxation therapy solely by monitoring the respiration of such subject in spite of the fact, as discussed below, that the various parameters of respiration have hitherto been thought to be so individual or particularized to a specific subject as to preclude generalizations with respect to respiratory parameters.

According to one aspect of the invention, the respiratory cycle T of a patient, including the time period $t_A$, corresponding to the inhalation/exhalation phase, and the time period $t_P$ corresponding to the pause or interval between inhalation/exhalation states is measured and the measured values of these time intervals $t_A$ and $t_P$ are formed into a quotient or ratio equal or related to $t_A/t_P$, an average value of which is determined over fixed period of no less than 0.5 minute to no more than 3 minutes for a given measurement and this average value as a qualitative measurement of relaxation is digitally displayed or further used or is displayed in an analog manner.

Utilizing the same principle and in an alternative approach to the present invention, for a given sequence of at least 5 at most 20 respiration cycles, each with a duration T, the respective time interval $t_A$ and the time interval $t_P$ for the inhalation/exhalation phase and the intervals between inhalation/exhalation phases are summed and the separately counted or summed intervals are formed into the ratio between the time interval $t_A$ and $t_P$ in a quotient-forming or dividing circuit and the quotient displayed digitally or in analog manner.

Both approaches are based upon our discovery that a psychophysical relaxation of the subject will give rise to a qualitative change in respiration in the sense that, with the increasing degree of relaxation, the intervals between inhalation/exhalation phases increase and indeed to the point that the ratio of the inhalation/exhalation phase interval to the pause interval will provide an objective measure of the degree of relaxation, whether averaged by taking a given number of such cycle measurements or summing the respective measurements over the fixed time period as stated.

Indeed, changes in the degree of relaxation can be monitored easily by monitoring the change in the ratio, i.e. as the ratio decreases, relaxation increases.

Thus, by displaying the quotient, or a value proportional or related in a given way to this quotient and changes thereof, it is possible to display electronically the relaxation state and changes thereof.

The method of the invention eliminates the effect of respiratory frequency and even respiratory amplitude. By taking the measurements over a given time period or by taking the measurements over a given number of respiratory cycles, both values effectively average out transient fluctuations in a respiratory functioning so that momentary disturbances in the respiration state do not falsify the results.

With the present invention, we can continuously record the changes in respiratory movements, in a numerical form and/or in the form of a curve.

The measurements of the time span $t_A$ of inhalation/exhalation and the interval $t_P$ between inhalation/exhalation phases can be directly made in terms of voltage values or electrical parameters proportional thereto which can be processed in conventional circuitry for electronic display.

To enable the display of the quotient or a value proportion thereto in an analog or digital form utilizing low cost equipment, it has been found to be advantageous to monitor the respective movements and convert these movements into analog voltage curves with the reference or baseline being selected so that the voltage curve represents a substantially alternating voltage with a positive amplitude segment with a peak amplitude A1 and a negative amplitude segment with a minimum A2, the duration of the inhalation/exhalation positive amplitude segment being represented by $t_1$ which is a major fraction of the total inhalation/exhalation phase.

In this case, the interval $t_2$ between a descending flank and an ascending flank of successive inhalation/exhalation phases, although not equal to the pause $t_P$ between inhalation/exhalation phases, will be sufficiently related to $t_P$ to enable a ratio to be formed and an average value of this ratio over at least 5 to at most 20 respiratory cycles or over a period of at least 0.5 minute to at most 3 minutes to be as quantatively as a measure of relaxation which can be displayed digitally or in an analog display. The area under the baseline for the respiration curve is the same as the area above the baseline over the inhalation/exhalation phase.

In this application of the process of the invention, the time period $t_1$ and $t_2$ in the relaxed state of the patient are largely equivalent, from the point of view of forming the ratio, the time period $t_A$ and $t_P$, respectively, as described. However, with decreasing relaxation, there is a progressively decreasing relationship between the values $t_1$ and $t_2$ and values $t_A$ and $t_P$ but even with reduced relaxation or until the patient is in a highly excited state, the relationship is sufficient to enable the quotient or its equivalent to be formed and having a meaningful relationship to relaxation.

It has been found to be especially advantageous when the respiratory movements are transformed into an alternating voltage to amplify the signal and filter it or transform it into a rectified or direct voltage signal so that the circuitry can provide a value $$\frac{(t_2 - t_1) \cdot C}{T}$$

where C is a constant and which is used as the average value which is digitally displayed or displayed in an analog manner.

In this variant of the process, a direct voltage signal is recovered from the alternating voltage signal, with a magnitude and polarity exclusively depending upon the ratio of the interval $t_1$ to $t_2$. This DC voltage signal can be displayed by analog or digital means, recorded (stored) or registered in some other fashion.

An apparatus for carrying out the method of this invention can include means for sensing the respiratory movements of the subject and for converting these respiratory movements into electrical voltage values. The circuitry may include a detector for converting the greater voltage change time interval and the substantially unchanged-voltage time interval into respective different electrical signals and means for averaging the respective signals and forming a ratio of the two signal groups upon averaging, over a given period of at least 0.5 to at most 3 minutes and a display for digitally or in an analog manner transisting the output of the latter circuit element.

Alternatively, means can be provided for transforming the voltage values representing respiration into alternating voltage segments with equal time-voltage flanks, e.g. an R-C network and an amplifier which can be connected to a comparator producing an output voltage of equal magnitude depending upon the polarity of voltage applied thereto, and a further R-C network connected to the comparator and generating the output to the display.

In another circuit arrangement according to the invention, the values of the inhalation/exhalation time durations and values of the pause durations between inhalation/exhalation phases are determined over 5 to 20 respiratory cycles and the ratio or an equivalent thereto is displayed.

BRIEF DESCRIPTION OF THE DRAWING

The above and other objects, features and advantages of the present invention will become more readily apparent from the following description, reference being made to the accompanying drawing in which.

SPECIFIC DESCRIPTION

Figure 7:
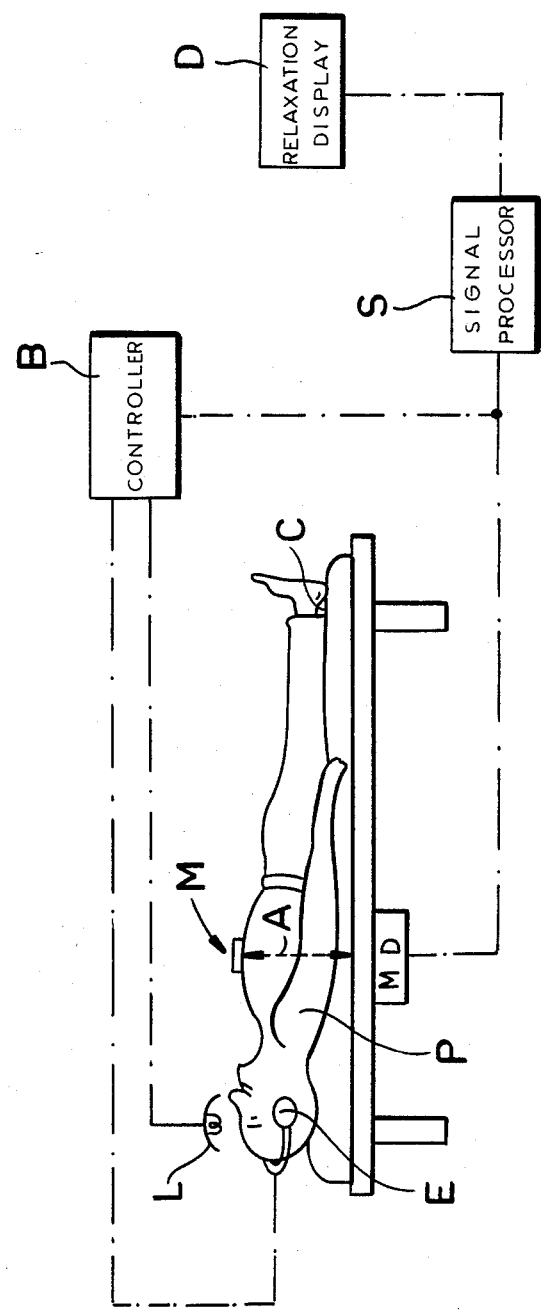
FIG. 7 is a diagram showing an application of the present invention.

Referring first to FIG. 7 it can be seen that relaxation/respiration therapy of a patient or subject P resting upon a couch C can utilize a pick-up arrangement M with a detector MD as described, for example in German patent document No. 31 09 026 to measure the respiratory movements A on inhalation and exhalation.

The output from the respiration and motion sensor in terms of electrical voltage signals (for example, see FIGS. 1 through 3) can be applied to a control unit B which generates, in turn, an optical signal which is applied to the lamp L and an acoustic signal which is applied to the earphones or headset E to provide the feedback previously mentioned. The feedback is designed to reduce muscular and brain activity and hence respiratory activity in accordance with the principles mentioned in the reference listed previously.

According to the present invention, in addition, a signal processor S (FIGS. 4 through 6) can be provided which receives these electrical voltages representing respiratory movement and, by processing them as described below in accordance with the invention, generates an analog digital output which is applied to a display D of the relaxation degree thereby permitting the therapist to properly control the apparatus B and fully evaluate the course of the treatment.

Figure 1:
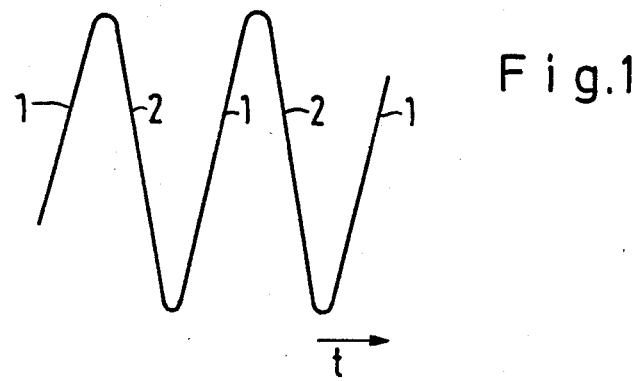
FIG. 1 is a graph showing a respiration curve of a subject in a nonrelaxed state without any baseline.
Figure 2:
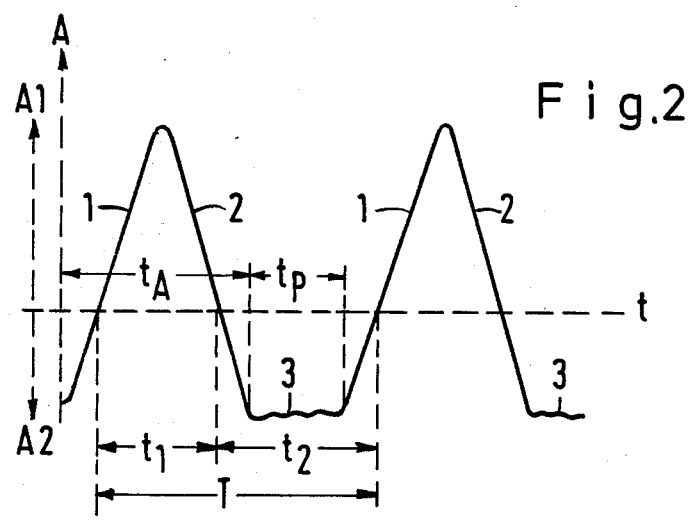
FIG. 2 is a graph of amplitude plotted along the ordinate versus time along the abscissa of the respiration curve of a subject in a relaxed state, showing the use of the principle developed above with respect to an alternating voltage to define the intervals and hence where the abscissa is a reference line between positive and negative amplitude portions of the curve.
Figure 3:
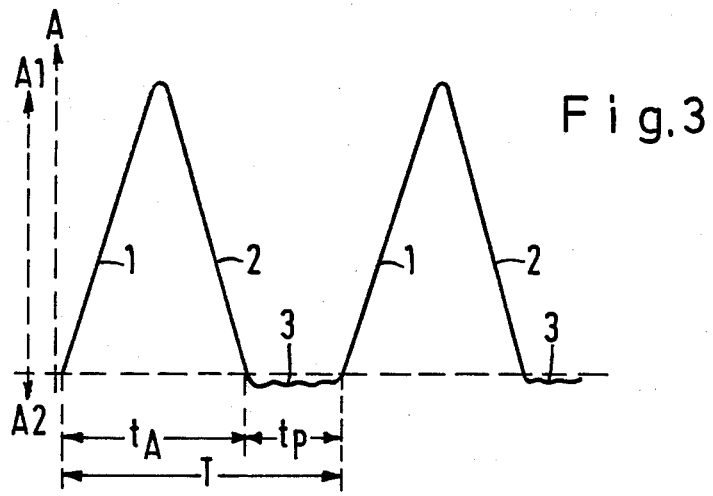
FIG. 3 is a graph showing another respiration curve for a relaxed subject in which the abscissa lies at a level equivalent to the baseline state at exhalation.

Referring now to FIGS. 1 through 3, it can be seen that FIG. 1 represents a rising flank of a voltage signal corresponding to inhalation while the reference numeral 2 represents the falling flank of a voltage signal representing exhalation. In FIG. 1 the respiration curve or characteristic shown to be practically a sinusoid corresponds to the respiration in a nonrelaxed or excited state of the subject.

As can be seen from FIGS. 2 and 3, in more relaxed states of the subject, there is after each inhalation/exhalation phase, in each respiration cycle, a pause or interval in which the subject rests in the exhalation condition before the next inhalation/exhalation phase. The segment of the curve representing this phase has been shown at 3 in these figures. As a consequence, in the relaxed respiration characteristic a segment 3 follows each inhalation rising flank and each exhalation falling flank in the aspiration cycle of total duration T.

As noted, for the measurement of the degree of relaxation or the extent of the relaxed state of the subject what is important is the ratio of the durations of the inhalation/exhalation phase on the one hand and the pause on the other.

Since there may be momentary perturbation in the respiratory activity of the individual, this ratio should be determined over a number of respiration cycles or over a time period each of which may be fixed for reproducibility so that, in effect, mean or average values of the ratio are utilized.

In FIG. 3, the duration of the inhalation/exhalation phase is represented as $t_A$ and the pause interval is represented as $t_P$. In each case, therefore $t_A+t_P=T$.

Figure 4:
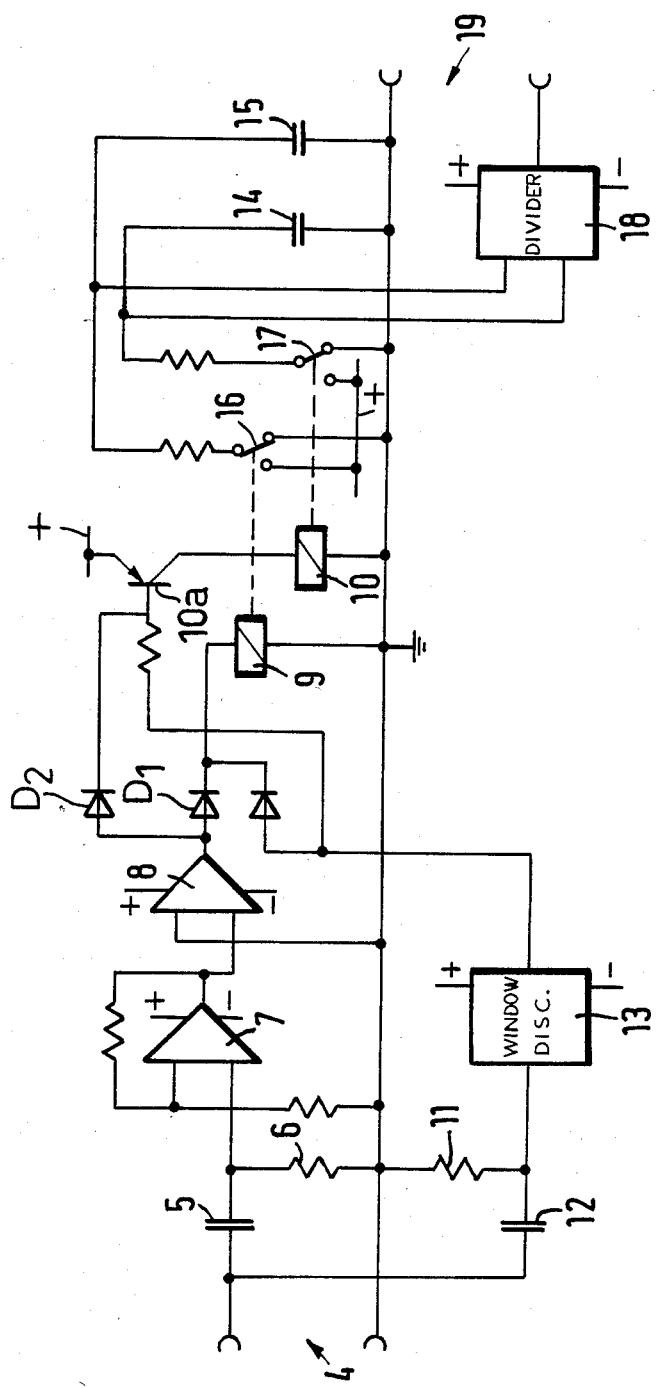
FIG. 4 is a circuit diagram for a circuit for processing the respiration signal corresponding to FIG. 3.

To provide a quantitative measurement which can be used for digital or analog display of the relaxation state, according to the invention, we may use the circuit shown generally in FIG. 4 which has a pair of input terminals 4 receiving the voltage signal from the respiration detector as previously described and one terminal of which can be considered at ground o zero potential; +12 volt and −12 volt inputs to the circuit elements have been indicated by plus (+) and minus (−) signs respectively.

This circuit is intended to process the respiration curve in accordance with FIG. 3 where the full values of the inhalation/exhalation duration $t_A$ and the pause duration $t_P$ are utilized as the essential durations.

A condenser 5 and a resistor 6 form a R-C network connected across the input terminals and thus form an integrator, the output of which is applied via an amplifier 7 to a comparator 8, the R-C network 5,6 supplying a direct voltage component to the output of the amplifier 7. The output of the comparator 8 is a signal which effectively represents the respiration phase itself, i.e. the rising and falling flanks 1 and 2 of the inhalation/exhalation phase. The output of the amplifier 8 is applied to a relay 9.

Another R-C network formed by a resistor 11 and a condenser 12 responds upon termination of the decay signal through a window discriminator 13 to operate a transistor 10a in circuit with a relay 10 so that the latter is switched to an ON-state when it is not blocked by the comparator 8 and thus the relay 10 is ON during the interval $t_P$.

During significant deviations of the respiration curve from the baseline (FIG. 3), i.e. during the time interval $t_A$, therefore, the relay 9 is ON while the relay 10 is blocked. Conversely, when the respiration curve is approximately at baseline, i.e. during the interval $t_P$, the relay 9 is deenergized and the relay 10 is active.

The relays 9 and 10 operate, in turn, switches 16 and 17 to allow charging of the storage capacitors 15 and 14, respectively, to accumulate charge in proportion to the respective time intervals for either the desired time period or the desired number of respiration cycles, thereby providing summed $t_A$ and summed $t_P$, values, $t_A$ and $t_P$, signals which are formed into the quotient $t_A:t_P$ in the divider 18.

The quotient which results is provided at 19 as an analog voltage output which can be directly recorded or displayed to represent the relaxation state.

An analog digital converter can be connected to the output 19 to provide a digital display or the quotient-forming circuit 18 can be digitally operated if a digital display or recordal is desired.

In practice, the signal applied to the input 4 varies in the range of ±1 volt whereby positive polarity indicates exhalation and negative polarity represents inhalation. The amplifier 7 can amplify the signal in correct phase relationship with an amplification factor of 10 so that its output is ±10 volt. The comparator 8 has about a +12 volt output when the output signal of the amplifier is negative. The relay 9 is energized through the diode $D_1$ while the relay 10 is blocked through the diode $D_2$.

The window discriminator has a negative voltage at its output over the duration $t_P$ and also very briefly between inhalation and exhalation. During the period $t_P$ the transistor is rendered conductive and relay 10 is energized.

During $t_A$ with relay 9 energized, condenser 15 charges while condenser 14 discharges and conversely during the interval $t_P$, relay 10 is energized to charge condenser 14 and discharge condenser 15.

Figure 5:
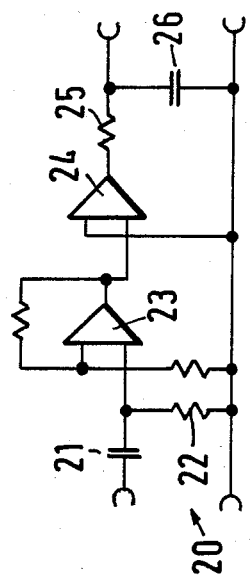
FIG. 5 is a circuit diagram of a circuit for processing the respiration signal of FIG. 2.

FIG. 5 shows a circuit for processing the respiration signal in accordance with the diagram of FIG. 2 and which is substantially simpler than the circuit of FIG. 4. In this circuit, as in FIG. 4, resistors which have not been identified are utilized only for bias and feedback purposes conventional in the art.

As can be seen from FIG. 2, the baseline of the respiration curve is set so that it lies substantially above the level of respiration voltage during the pause. As a consequence, the inhalation/exhalation phase is transected by the baseline so that the areas above the baseline and below the baseline within the envelope of the inhalation/exhalation phase are substantially equal.

The baseline crossings of the inhalation and exhalation flank 1 and 2 are here separated by a time interval $t_1$ during the period $t_A$ and the overall respiration amplitude A is divided into two segments $A_1$ above the baseline and $A_2$ below the baseline.

An interval $t_2$ can be measured between the descending flank of one inhalation/exhalation phase and the ascending flank of the next as previously described. The values $t_1$ and $t_2$ have sufficient correlation with the $t_A$ and $t_P$ that they can be used to evaluate the relaxation state in cases in which $t_1$ deviates from $t_2$ to indicate some degree of relaxation.

The voltage curve is applied at the input terminals 20 of FIG. 5 to a R-C network formed by a condenser 21 and resistor 22 which transforms the curve into an AC voltage applied to the amplifier 23 which is connected to a comparator 24 whose output is a positive or negative voltage of given magnitude depending upon the polarity of the signal received from the amplifier. These voltages are applied via a resistor 25 and condenser 26 to the output terminals, the condenser having a voltage thereacross which is proportional to the value $$\frac{(t_2 - t_1) \cdot C}{T}$$

where C is a constant and all other terms have been previously defined. This voltage can be directly displayed as an analog indication of the degree of relaxation or via an analog/digital converter displayed in a digital format or via conventional electronic processing circuits can be stored and recalled from memory.

Figure 6:
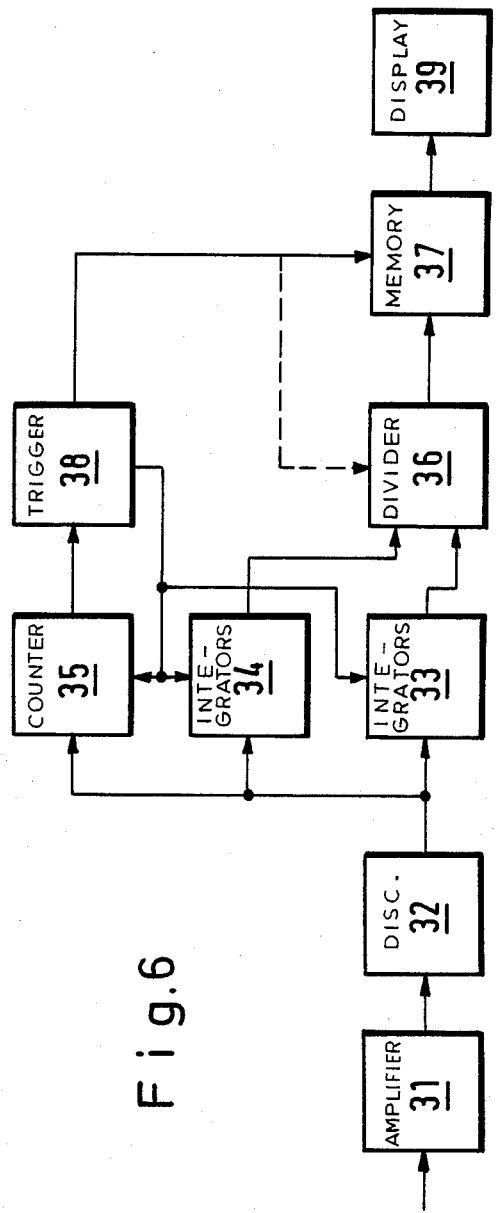
FIG. 6 is a block diagram of a circuit for processing a respective signal in accordance with other principles of the invention described above.

FIG. 6 shows a circuit for evaluating the respiration curve for a given number of respiration cycles between 5 and 20.

The respiration movement signal is applied to the input of an amplifier 31 which delivers its output to a discriminator distinguishing between the portions of the signals corresponding to the times $t_A$ and $t_P$. The output of the discriminator 32 is applied to the integrators 33 and 34 which respectively sum magnitudes representing the duration $t_A$ and $t_P$ and the summed values are delivered to the divider or quotient former 36 which generates the ratio of the summed values.

Since the value is only meaningful for the desired number of cycles, ahead of the display or registering unit 39, a storage circuit 37 is provided which retains the previous value until a new value is delivered. A counter 35 counts the number of respiration cycles and operates a trigger circuit 38 to transfer the memory to the display and cancel an previously stored signal, and to transfer the integrated values to the divider when the desired number of respiration cycles are counted. The trigger circuit 38 also resets the counter to zero to begin a new count of a fresh sequence of respiration cycles.

The circuit elements 33 through 37 can be replaced, of course, by a programmable unit such as a microprocessor and it may not be necessary to continuously determine the ratio, since one may wish to monitor the ratio only at selected times (as represented by the broken line controlling the divider).

It is also possible without the circuit to average a number of ratios of given numbers of individual respiration cycles and thereby form the average value for a given number of cycles in accordance with the present invention.

We claim:

1. A method of measuring a degree of relaxation of a subject which comprises the steps of:
    measuring respiration movements of said subject and generating a respiration signal representing an inhalation/exhalation phase and an interval between inhalation/exhalation phases for each respiration cycle;
    averaging time durations related to a duration $t_A$ of inhalation/exhalation phase and a duration $t_P$ of said interval for a number of respiration cycles of duration T where $T = t_A + t_P$; and
    forming an average quotient of durations $t_P$ and $t_A$ and displaying a value related to said quotient as a qualitative measurement of the degree of relaxation of said subject.

2. The method defined in claim 1 wherein values corresponding to the duration $t_A$ and $t_P$ are averaged for respiration cycles over equal time durations between 0.5 minute to 3 minutes to provide said qualitative measurement.

3. The method defined in claim 1 wherein a baseline level is established for said respiration signal, such that intersections of successive rising and falling flanks of said signal during the inhalation/exhalation phase with the baseline are separated by a time interval $t_1$ and intersections of successive falling and rising flanks with said baseline level are separated by a time interval $t_2$, the relative durations $t_2$ and $t_1$ being ascertained to form said qualitative measurement.

4. The method defined in claim 3 wherein the durations $t_1$ and $t_2$ are ascertained for at least 5 and at most 20 respiration cycles to obtain said qualitative measurement.

5. The method defined in claim 3 wherein the durations $t_1$ and $t_2$ are ascertained for a number of respiration cycles over fixed durations between 0.5 and 3 minutes for said qualitative measurement.

6. The method defined in claim 3 wherein said durations are formed into a direct voltage output signal in accordance with the formula $$\frac{(t_2 - t_1) \cdot C}{T}$$

where C is a constant, and a signal corresponding to the value of said formula is displayed as at said qualitative measurement.

7. The method defined in claim 1 wherein said qualitative measurement is displayed in an analog display.

8. The method defined in claim 1 wherein said qualitative measurement is displayed in a digital display.

9. The method defined in claim 1 wherein values of $t_A$ and $t_P$ are measured over fixed numbers of respiration cycles of duration T between 5 and 20 in number, to obtain each such qualitative measurement.

10. An apparatus for measuring the relaxation state of a subject which comprises:
    means for detecting respiration movements of said subject and generating a respiration signal having an inhalation/exhalation phase of duration $t_A$, separated at least during relaxation of the subject by an interval of duration $t_P$ from a subsequent respiration cycle having a duration $T = t_A + t_P$;
    signal processing means connected to said detecting means for evaluating a ratio between a value related to the duration $t_A$ to a value related to the duration $t_P$ over a period of at least a number of respiration cycles to form an output representing a qualitative measurement of relaxation state; and
    display means for displaying a value corresponding to said output.

11. The apparatus defined in claim 10 wherein said signal processing means comprises means for distinguishing between different signals corresponding respectively to $t_A$ and $t_P$, averaging said different signals, and forming a ratio of the averaged difference signals over a fixed time period of at least 0.5 minute and at most 3 minutes.

12. The apparatus defined in claim 10 wherein said signal processing means includes a R-C network connected to an amplifier, a comparator connected to said amplifier and generating equal magnitude voltages of positive and negative polarity in dependence upon the polarity of the output of said amplifier, and a further RC-network forming an output element connected to said display means.

13. The apparatus defined in claim 10 wherein said signal processing means includes means responsive to said respiration signal for generating distinct signals related to the durations $t_A$ and $t_P$, means for summing the respective distinct signals, means for forming a quotient of the sums of said distinct signals relating to the durations $t_P$ with the sums of said distinct signals relating to the duration $t_A$, and counting means for fixing the number of signals counted at a number between at least 5 and at most 20 for each qualitative measurement and display of relaxation degree.

14. The apparatus defined in claim 10 wherein said means is a digital display.

15. The apparatus defined in claim 10 wherein said display means is an analog display.

* * * * *